United States Patent
Ota

(10) Patent No.: US 6,652,512 B2
(45) Date of Patent: Nov. 25, 2003

(54) LASER TREATMENT APPARATUS

(75) Inventor: Yasuo Ota, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 09/878,428

(22) Filed: Jun. 12, 2001

(65) Prior Publication Data

US 2001/0053907 A1 Dec. 20, 2001

(30) Foreign Application Priority Data

Jun. 16, 2000 (JP) ......................................... 2000-185938

(51) Int. Cl.[7] ................................................ A61B 18/20
(52) U.S. Cl. ............................. 606/12; 606/3; 606/13; 606/17
(58) Field of Search ..................... 606/3, 5, 10–13, 606/17

(56) References Cited

U.S. PATENT DOCUMENTS

| | | | |
|---|---|---|---|
| 4,069,823 A | * | 1/1978 | Isakov et al. ................... 606/11 |
| 4,388,924 A | | 6/1983 | Weissman et al. |
| 5,098,426 A | * | 3/1992 | Sklar et al. ..................... 606/5 |
| 5,408,409 A | | 4/1995 | Glassman et al. |
| 5,489,758 A | | 2/1996 | Nihei et al. |

FOREIGN PATENT DOCUMENTS

| | | |
|---|---|---|
| EP | 0 880 941 A1 | 12/1998 |
| EP | 1 031 324 A1 | 8/2000 |
| WO | WO 99/07438 | 2/1999 |

* cited by examiner

Primary Examiner—David M. Shay
(74) Attorney, Agent, or Firm—Oliff & Berridge, PLC

(57) ABSTRACT

A laser treatment apparatus for irradiating a treatment part with a laser beam for treatment is disclosed. The apparatus includes a treatment light irradiation unit including a treatment light source which emits the treatment laser beam, an irradiation optical system which delivers the treatment laser beam emitted from the light source to irradiate the treatment part, and a laser emission end unit internally provided with a part of the irradiation optical system. The apparatus further includes a movement unit which moves the emission end unit with respect to the treatment part, a determination unit which determines an irradiation position of the treatment laser beam, and a control section which transmits a control signal to the movement unit based on a determination result by the determination unit and controls laser irradiation.

6 Claims, 10 Drawing Sheets

SKIN SURFACE

LASER TREATMENT APPARATUS

BACKGROUND OF THE INVENTION

1. Field of the Invention

The present invention relates to a laser treatment apparatus for irradiating a skin with a laser beam for treatment.

2. Description of Related Art

There has been known a laser treatment apparatus for irradiating a skin of a patient with a laser beam for treatment (hereinafter referred to as a treatment beam) to remove birthmarks, stains, tattoos being on the skin or to cause depilation. A type of this apparatus is provided with a handpiece that houses an optical system for irradiation of a treatment beam. This handpiece is designed to be directly held by an operator for operations. Thus, the operator can carry out laser irradiation (with a treatment beam) on a treatment part of the skin while manually moving the handpiece. Recently, some handpieces are provided with peripheral devices such as a scanner for scanning a treatment beam and a cooler for cooling the treatment part.

However, it would be difficult for the operator to perform the laser irradiation by means of the handpiece while moving it by hand with respect to different parts of a patient's body to be treated. The operator is occasionally forced to carry out the treatment in an unnatural position depending on a body part of a patient.

Furthermore, the hand piece provided with peripheral devices such as a scanner and a cooler is hard to handle due to its size and weight. Consequently, the burden on the operator would increase and the laser irradiating operation could not be adequately carried out.

SUMMARY OF THE INVENTION

The present invention has been made in view of the above circumstances and has an object to overcome the above problems and to provide a laser treatment apparatus enabling an operator to perform laser irradiation with ease and less burden on him.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is a laser treatment apparatus for irradiating a treatment part with a laser beam for treatment, the apparatus including: a treatment light irradiation unit including: a treatment light source which emits the treatment laser beam; an irradiation optical system which delivers the treatment laser beam emitted from the light source to irradiate the treatment part; and a laser emission end unit internally provided with a part of the irradiation optical system; a movement unit which moves the emission end unit with respect to the treatment part; a determination unit which determines an irradiation position of the treatment laser beam; and a control section which transmits a control signal to the movement unit based on a determination result by the determination unit and controls laser irradiation.

According to another aspect of the present invention, there is provided a laser treatment apparatus for irradiating a treatment part with a laser beam for treatment, the apparatus including: a treatment light irradiation unit including: a treatment light source which emits the treatment laser beam; an irradiation optical system which delivers the treatment laser beam emitted from the light source to irradiate the treatment part; and a laser emission end unit internally provided with a part of the irradiation optical system; a first movement unit which moves the emission end unit to change an inclination angle of a laser emission direction of the emission end unit with respect to the treatment part; a second movement unit which moves the emission end unit to change a position of the emission end unit in a two-dimensional direction parallel to a reference plane with respect to the treatment part; a third movement unit which moves the emission end unit to change a distance from the emission end unit to the treatment part in the laser emission direction; and a determination unit including: an angle detection unit which detects the inclination angle of the laser emission direction of the emission end unit with respect to the treatment part; a position detection unit which detects the position of the emission end unit in the two-dimensional direction parallel to the reference plane with respect to the treatment part; a distance detection unit which detects the distance from the emission end unit to the treatment part in the laser emission direction; and a determination section which determines an irradiation position of the treatment laser beam so that the inclination angle of the emission end unit in the laser emission direction becomes substantially perpendicular to the treatment part and the treatment laser beam comes in focus on the treatment part; and a control section which transmits a control signal to at least one of the movement units based on a determination result by the determination unit and controls laser irradiation.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
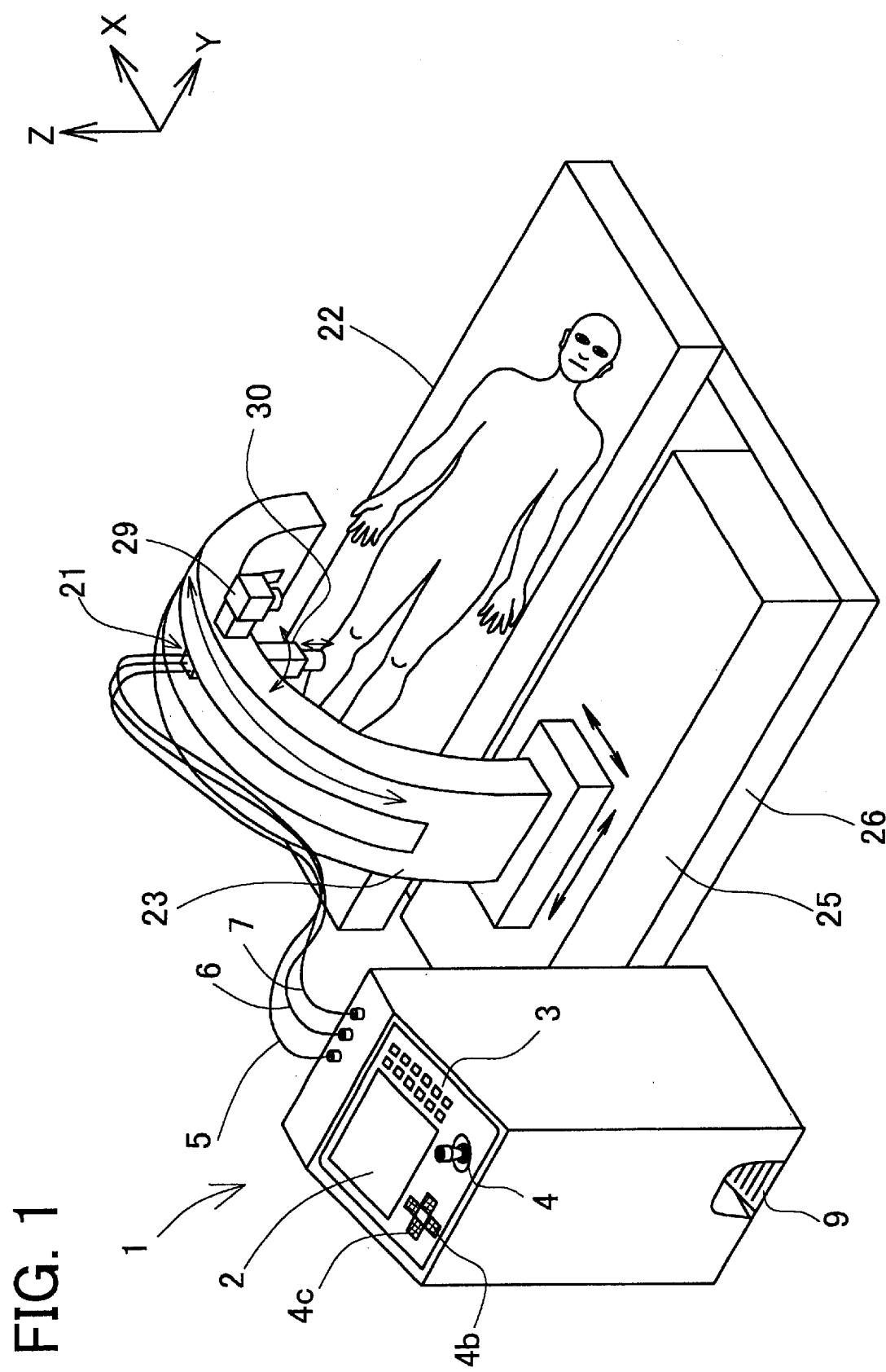
FIG. 1 is a perspective view of a laser treatment apparatus in an embodiment according to the present invention.
Figure 2:
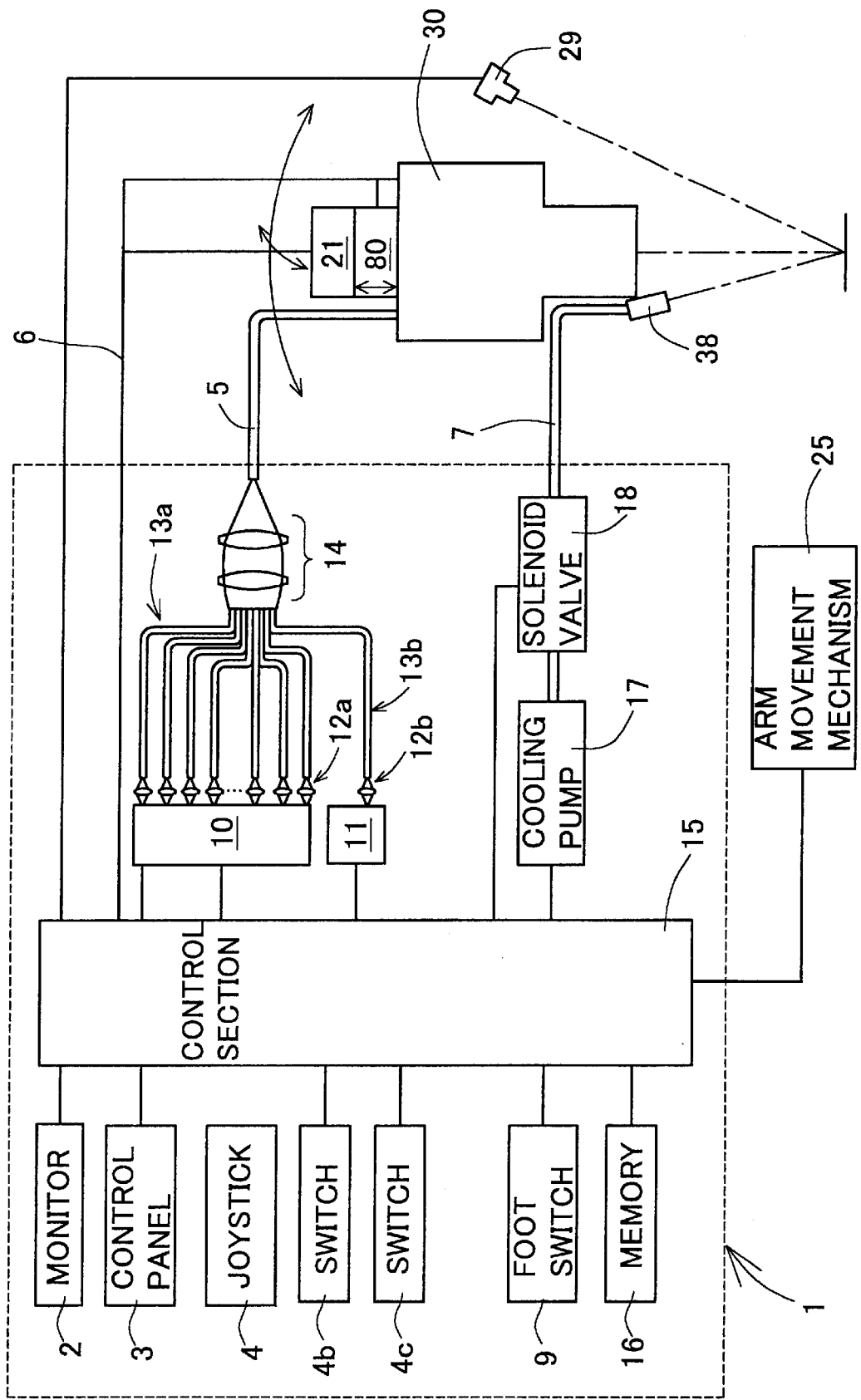
FIG. 2 is a schematic structural view of a control system and a drive system in the apparatus.

A detailed description of a preferred embodiment of a laser treatment apparatus embodying the present invention will now be given referring to the accompanying drawings. FIG. 1 is a perspective view of a laser treatment apparatus (a laser depilation apparatus in the present embodiment) used for the whole body skin of a patient. FIG. 2 is a schematic structural view of a control system and a drive system of the apparatus.

Numeral 1 is a main unit of the laser apparatus. This main unit 1 houses a control section 15, a light source section 10 which emits a laser light beam for treatment (a treatment beam), a light source 11 which emits an aiming light beam (an aiming beam), a cooling pump 17, and others.

Numeral 22 is a bed on which a patient lies down and it is fixed on a base 26. At the side of the bed 22 is arranged an arcuate arm 23 which supports a laser emission end unit 30. The arm 23 is mounted on the base 26 to be movable in a Y-direction, or a longitudinal direction of the bed 22, and in an X-direction, or an orthogonal direction to the longitudinal direction. Numeral 25 is an arm movement mechanism for moving the arm 23 in the X- and Y-directions. This mechanism 25 is provided therein with an XY stage, a motor for driving the XY stage, and others. The mechanism 25 has often been used as an XY stage and therefore a detailed explanation thereof is omitted in the present embodiment. It is to be noted that an alternative design is to move the bed 22 in the X- and Y-directions instead of moving the arm 23. A further alternative design is to move both the arm 23 and the bed 22 in the X- and Y-directions.

A treatment beam and an aiming beam from the main unit 1 are delivered to the emission end unit 30 through a fiber cable 5. The emission end unit 30 is supported on the arm 23 at an inclination angle of a direction of emission of the laser beams (a laser emission direction), namely, a Z-direction, which is changeable. The Z-direction in the present specification means the direction in which a distance from the unit 30 to a patient's body changes, and also the direction of the optical axis of a lens 37. The inclination angle is adjusted by an X- and Y-directions movement (rock) mechanism 21 provided on the arm 23. The arm 23 is also provided with a Z-direction movement mechanism 80 for changing the distance in the laser emission direction from the unit 30 to the patient who lies down on the bad 22. The X- and Y-directions movement mechanism 21 and the Z-direction movement mechanism 80 will be mentioned later in detail.

A camera 29 for observation is fixed to the arcuate arm 23 at a nearly center position thereof. This camera 29 is used for taking (photographing or imaging) an image of the treatment part in a wide area.

The main unit 1 is further provided with a control panel 3 and a monitor 2. The control panel 3 is used for inputting various settings; ON/OFF of emission of the aiming beam, laser irradiation conditions such as output power of the treatment beam, shape of a scanning pattern, irradiation time, etc., and conditions for movement of the emission end unit 30. The monitor 2 displays images of the treatment part to be observed and the various conditions set on the control panel 3. To be more specific, the monitor 2 displays both the image taken by the camera 29 and a magnified image of the treatment part taken by a camera 31 mentioned later.

Numeral 4 is a joystick for issuing a drive command to the X- and Y-directions movement mechanism 21. Numeral 4c is a switch (button) for issuing a drive command to the arm movement mechanism 25 to move the arm 23 in a Y-direction. Numeral 4b is a switch (button) for issuing a drive command to the arm movement mechanism 25 to move the arm 23 in an X-direction. Numeral 9 is a footswitch for transmitting a trigger signal to start laser irradiation.

Between the main unit 1 and the emission end unit 30, there are connected, besides the fiber cable 5, an electric cable 6 and a tube 7 for delivering cooled, compressed air from the cooling pump 17 to the unit 30. As shown in FIG. 2, a cooled-air ejection nozzle 38 is attached to the tip end of the emission end unit 30 to eject cooled air for cooling the treatment part. Opening a solenoid valve 18 disposed in the main unit 1 allows the cooled, compressed air to be delivered from the cooling pump 17 to the ejection nozzle 38 through the tube 7. The compressed air is thus ejected toward the treatment part.

The light source section 10 consists of a plurality of laser diodes. Each laser beam emitted from the laser diodes is focused on each end face of fibers 13a through condensing lenses 12a disposed in a one-to-one correspondence with the fibers 13a. On the other hand, the output end face sides of the fibers 13a are bundled, thereby combining the laser beams emitted from the laser diodes into a laser beam with high power to be used as a treatment beam. The treatment beam in the present embodiment is near infrared light of wavelengths from 800 to 820 nm.

The aiming beam emitted from the light source 11 is condensed onto an end face of a fiber 13b through a condensing lens 12b, then entering the fiber 13b. The output end face side of the fiber 13b is bundled with the output end face sides of the fibers 13a, causing the aiming beam emerged from the fiber 13b to go through in the same optical path as that of the treatment beam. The aiming beam in the present invention is red visible light of wavelengths from 620 to 650 nm.

The treatment beam and the aiming beam which are emerged from the output end faces (a fiber bundle part) of the fibers 13a and 13b bundled together are condensed through a group of condensing lenses 14, entering the fiber cable 5. Through this fiber cable 5, the treatment beam and the aiming beam are delivered to the laser emission end unit 30.

Figure 3:
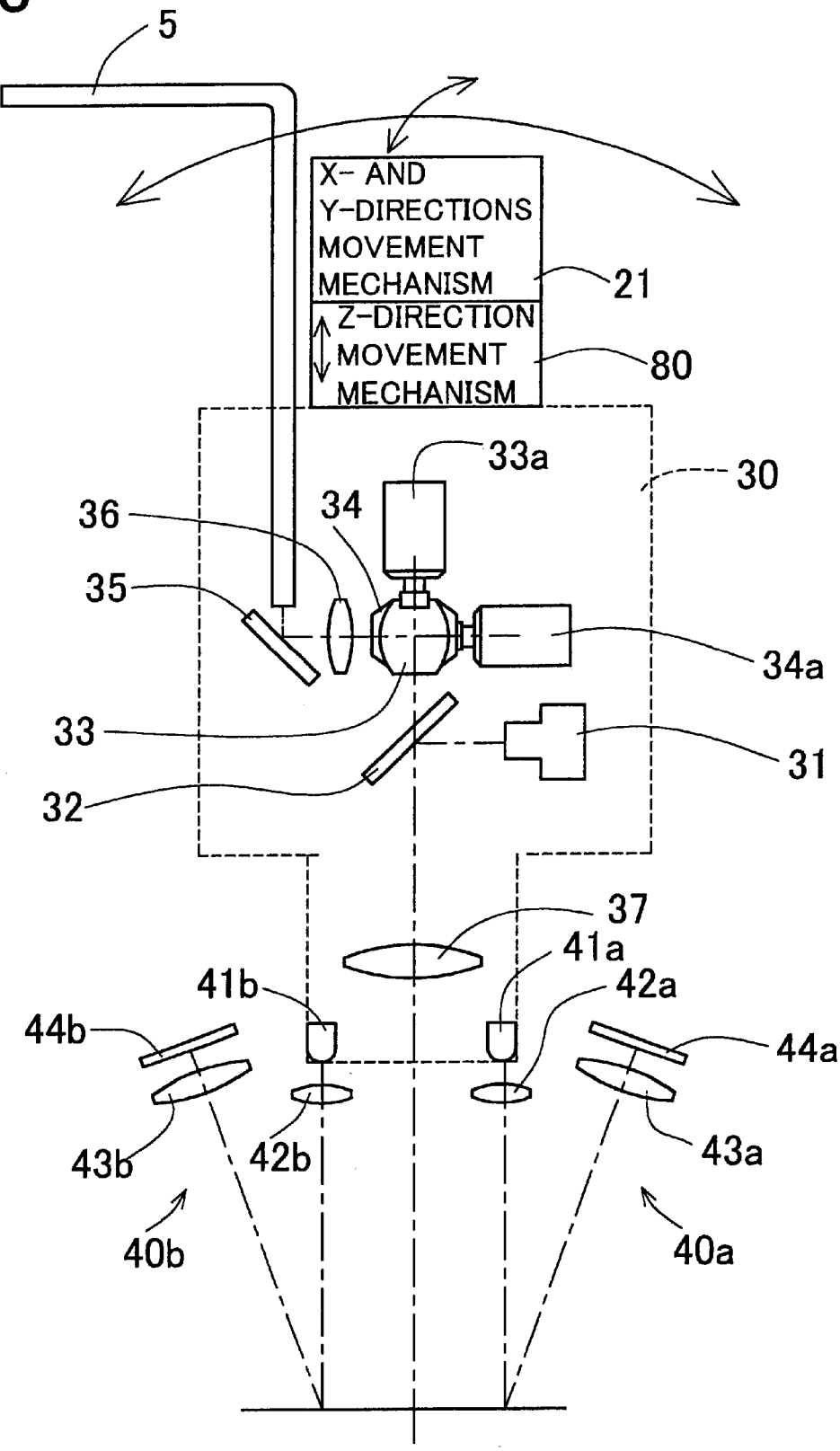
FIG. 3 is a schematic structural view of an optical system and a drive system therefor in the apparatus.

A laser irradiation optical system disposed in the emission end unit 30 is explained below with reference to FIG. 3. The emission end unit 30 is provided with a first galvano mirror 33 and a second galvano mirror 34. These mirrors 33 and 34 are caused to rotate (swing) by operation of a first and second galvano motors 33a and 34a respectively. The swinging mirrors 33 and 34 deflect the treatment beam (and the aiming beam) to shift an irradiation position (the position of a spot) in an X- and Y-directions, scanning the area within the shape of a determined scanning pattern. In other words, the treatment beam (and the aiming beam) having entered the laser emission end unit 30 through the fiber cable 5 is deflected by a mirror 35 and collimated by a collimator lens 36. Sequentially, the collimated light is deflected in the X- and Y-directions by operation of the first and second galvano mirrors 33 and 34 and then is focused into a spot of about 5 mm in diameter on the treatment part (a skin surface) in a predetermined focal position by a condensing lens (a focusing lens) 37. The first and second mirrors 33 and 34 are controlled to swing at angles set based on the shape of the determined scanning pattern, shifting (scanning) the irradiation position (the spot position) of the treatment beam (and the aiming beam). It is to be noted that when a scanning switch (button) on the control panel 3 is turned OFF, the first and second mirrors 33 and 34 are returned to come to rest at respective initial positions (angles), so that the mirrors 33 and 34 at rest deflect the treatment beam (and the aiming beam) in the direction of the optical axis of the lens 37.

A dichroic mirror 32 is disposed in the optical axis of the lens 37. A camera 31 is arranged in a position to which the dichroic mirror 32 reflects reflection light from the treatment part. The photographing (imaging) optical axis of the camera 31 is made coaxial with the optical axis of the lens 37 by the dichroic mirror 32. The camera 31 takes (photographs or images) a picture image of the treatment part in a magnified form and the monitor 2 displays the taken image. The operator therefore can observe pre-, in-, and post-operative conditions of the treatment part.

Figure 4:
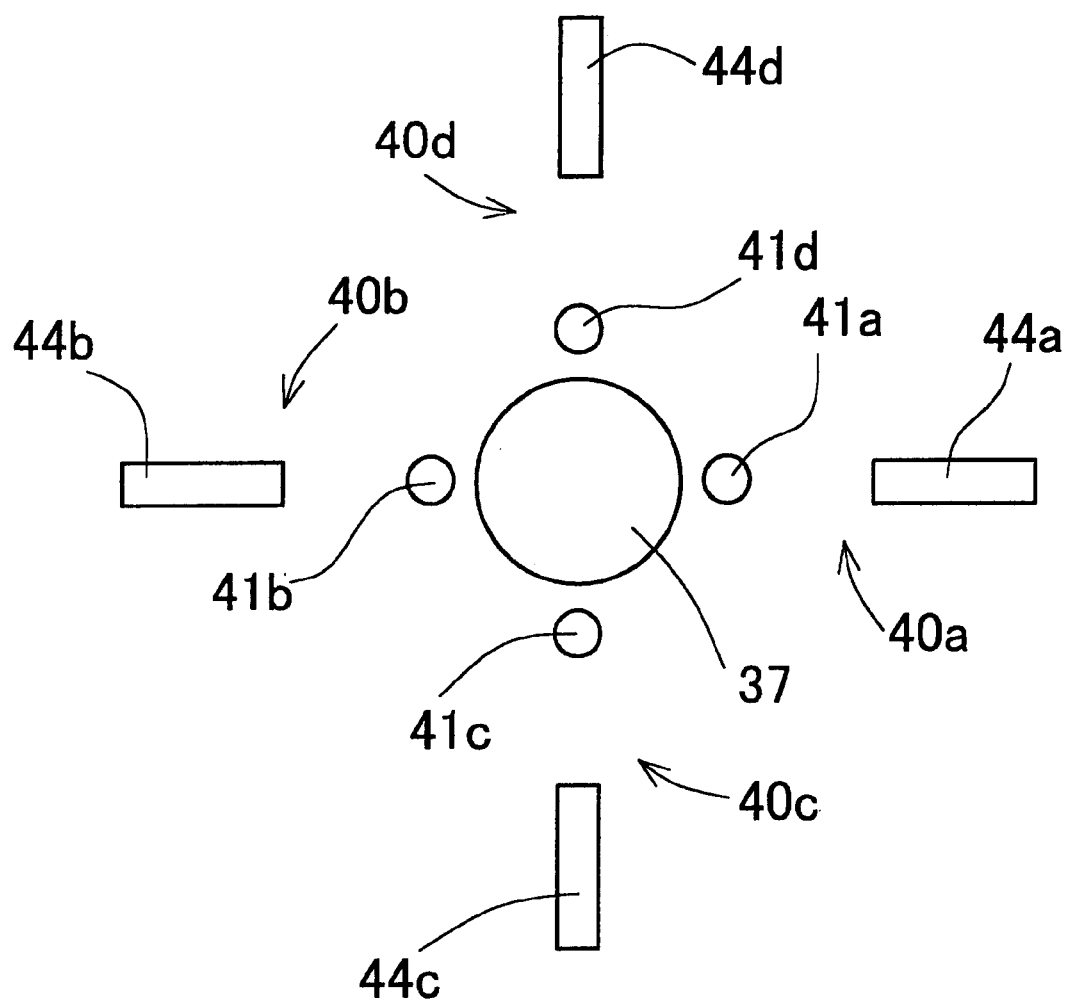
FIG. 4 is an explanatory view showing placement of four sets of focal alignment sensor sections.

In the tip end of the laser emission end unit 30, there are provided four sets of focal alignment sensor sections 40a, 40b, 40c, and 40d. As shown in FIG. 4, the sensor sections 40a–40d are equally, circumferentially spaced around the optical axis of the lens 37, or arranged two each at symmetrical positions about the optical axis so that two imaginary lines each connecting the symmetrical two are orthogonal to each other. Each of the sensor sections 40a–40d has a structure generally used as the principles of auto focusing. In a sensor section 40a, one of the four sets, a spot light of an infrared LED 41a is projected by a lens 42a to the plane of a target object and the reflection light therefrom is imaged by a linear CCD 44a through a lens 43a. Based on the location of the spot image formed on the linear CCD 44a, it is detected as to whether the object (skin surface) is nearer or farther than the focal point (focal plane) of the treatment beam and as to a distance from the LED 41a (the emission end unit 30) to the object. The other sensor sections 40b–40d each have the same configuration as the above mentioned sensor section 40a, the sections 40c and 40d being unillustrated in FIG. 3. When the LED 41a–41d are controlled to light up in turn, the corresponding linear CCDs 44a–44d detect respective distances.

Figure 5:
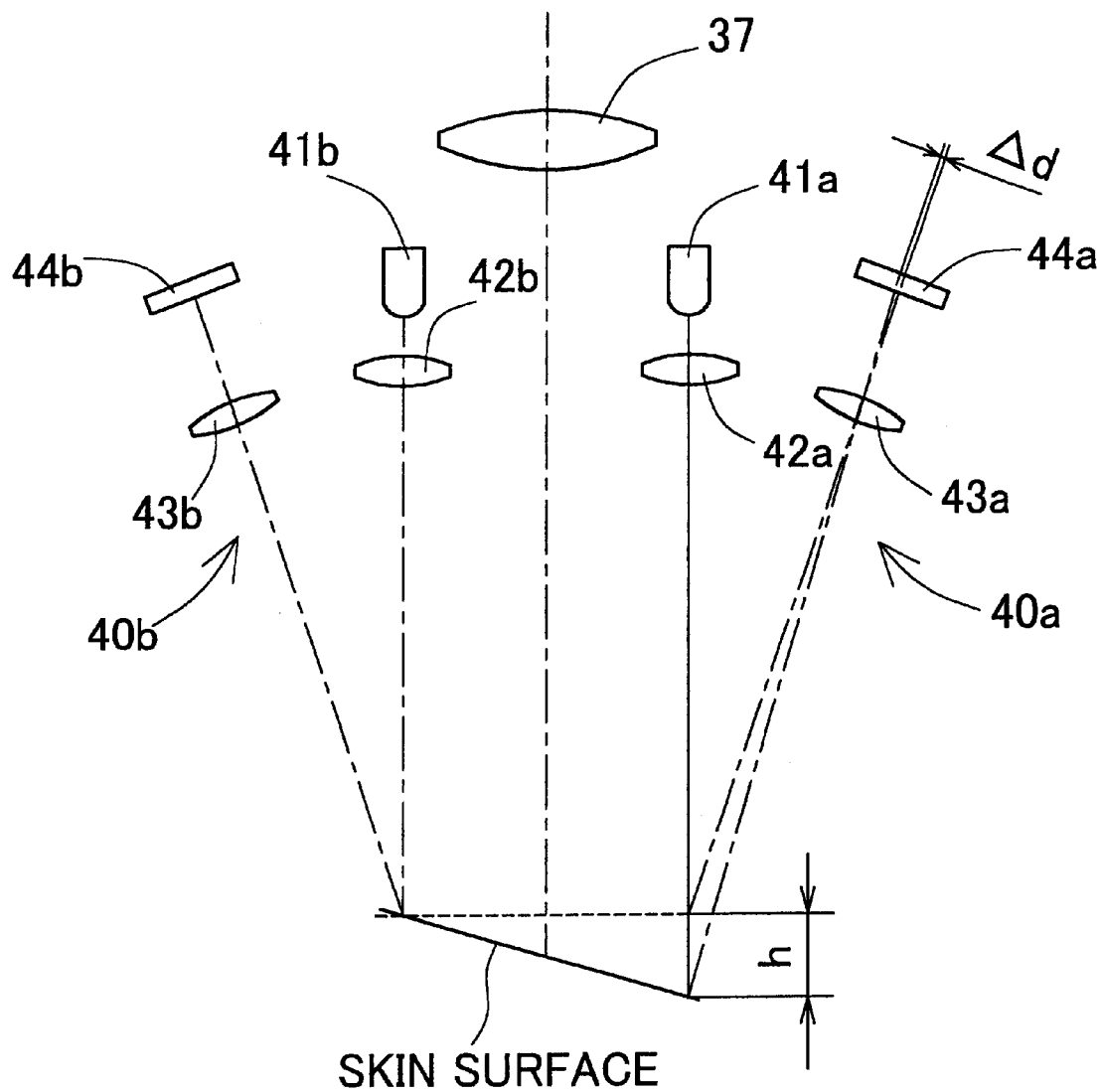
FIG. 5 is an explanatory view showing how to detect a slant of a skin surface by means of the four sets of focal alignment sensor sections.

The sensor sections 40a–40d configured as above jointly construct an inclination sensor for detecting an inclination angle of the laser emission direction (Z-direction) of the unit 30 with respect to the treatment part (the skin surface). To be more specific, as shown in FIG. 5, if the skin surface is slant, not vertical, with respect to the optical axis of the lens 37, the spot image of the LED 41a is farther than that of the LED 41b, so that the CCD 44a receives light (the image) at a position displaced by an amount Δd. The displacement direction and amount Ad of this light-receiving position show that the spot image of the LED 41a is farther by a distance h than that of the LED 41b. Thus, the relation between the two positions indicates how slant the skin surface is. When the above detection is performed on four spot images respectively, a three-dimensional slant of the surface surrounded by the four spot images can be determined.

Figure 6:
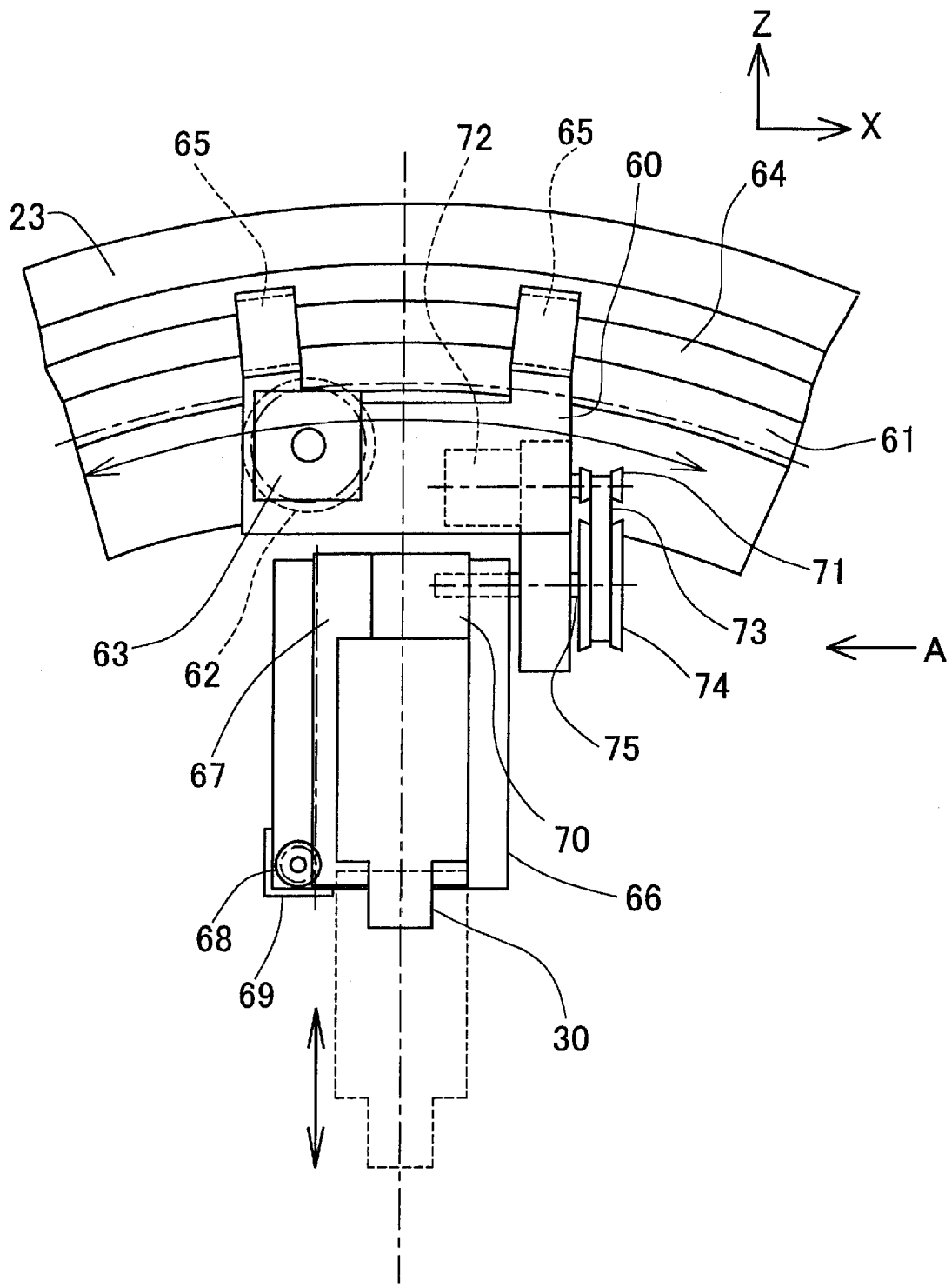
FIG. 6 is a schematic structural view of an X- and Y-directions movement (rock) mechanism and a Z-direction movement mechanism.
Figure 7:
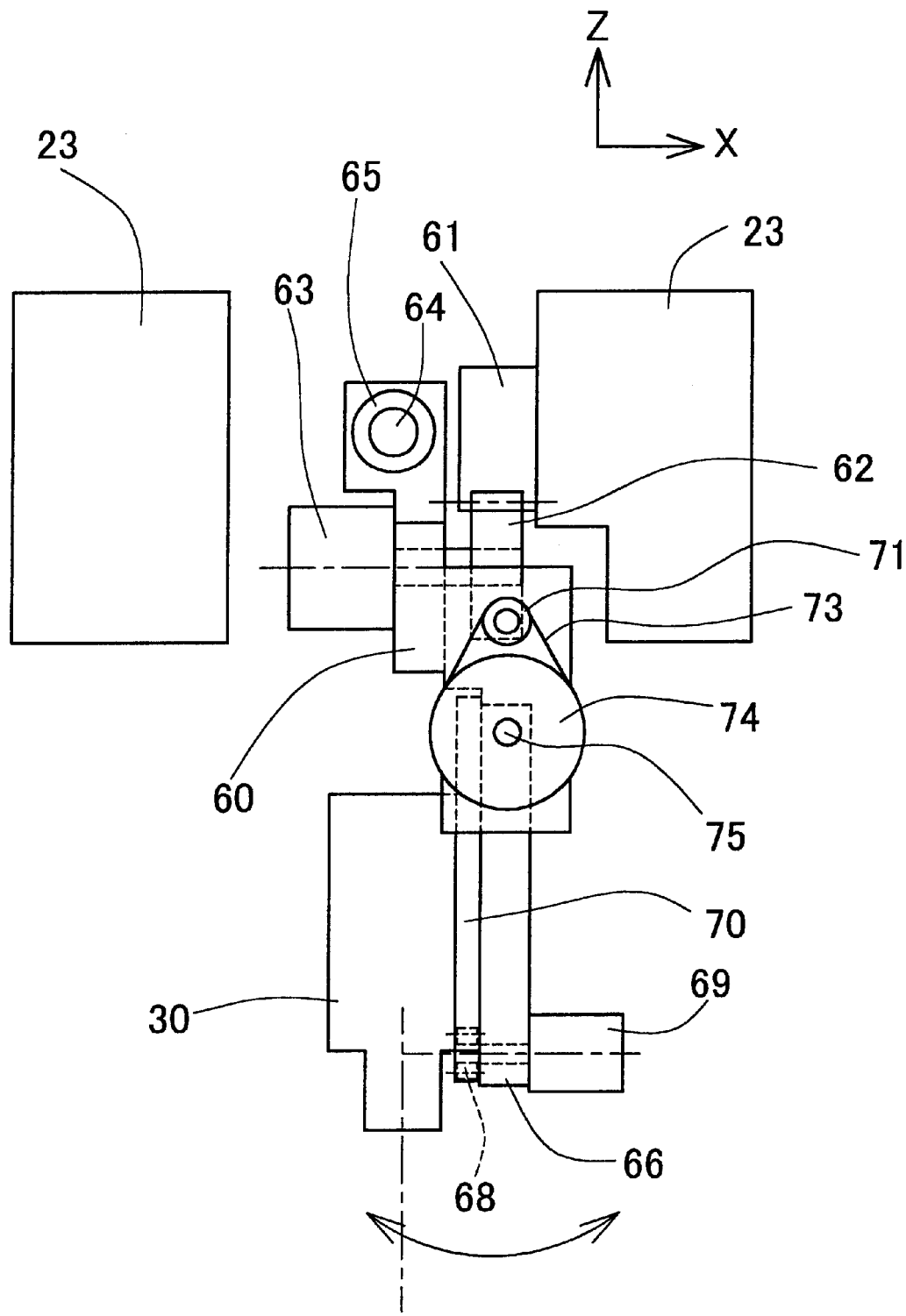
FIG. 7 is a schematic structural view of the X- and Y-directions movement (rock) mechanism and the Z-direction movement mechanism of FIG. 6.

Next explanation is made on the movement mechanism 21 and the movement mechanism 80, referring to FIGS. 6 and 7. FIG. 6 is a schematic structural view of the X- and Y-directions movement mechanism 21 and the Z-direction movement mechanism 80. FIG. 7 is a schematic structural side view of those in FIG. 6.

An X-direction movement (rock) system of the movement mechanism 21 is first described below. Numeral 64 is a shaft rail attached to the arcuate arm 23, extending in a semicircular form along the arm 23. Two ball bushes 65 are slidably fit on the rail 64. These bushes 65 are fixed to a rock base 60. Numeral 63 is a motor for the X-direction movement (rock). This motor 63 is mounted on the rock base 60 and has a driving shaft which is engaged with a pinion 62. Numeral 61 is a rack of a semicircular form being concentric with the rail 64. This rack 61 is fixed to the arm 23. Driving force of the motor 63 causes the rotation of the pinion 62 in engagement with the rack 61, thereby moving the base 60 along the semicircular rail 64. The emission end unit 30 is arranged in the lower side of the base 60, so that it will also be moved along the rail 64. Consequently, the emission end unit 30 is caused to move (rock) in the X-direction.

A Y-direction movement (rock) system of the movement mechanism 21 is explained below. A motor 72 for the Y-direction movement (rock) is attached to the base 60 and has a driving shaft on which a pulley 71 is fixedly fit. The driving force of this motor 72 is transmitted to a pulley 74 through a belt 73 wound on the pulleys 71 and 74, as shown in FIG. 6. The pulley 74 is fixed to an end of a shaft 75 that is rotatably supported in the base 60. Another end of the shaft 75 is fixed to a vertical base 66. Accordingly, when the motor 72 is driven, the base 66 is moved (rocked) in the Y-direction by means of the pulleys 71 and 74 and the belt 73, causing the emission end unit 30 disposed on the base 66 to move (rock) in the Y-direction.

Next, the movement mechanism 80 is explained. A vertical rail 70 is attached onto the base 66 so that the emission end unit 30 is movable on the rail 70 in the up-and-down direction (Z-direction). A motor 69 for the Z-direction movement is mounted on the base 66 and has a driving shaft on which a pinion 68 is fixedly fit. A rack 67 is attached to the emission end unit 30 and is engaged with the pinion 68. Accordingly, the driving force of the motor 69 causes the emission end unit 30 to move by means of the rack 67 and the pinion 68 in the up-and-down (Z-) direction. This allows change in distance from the emission end unit 30 to the patient's body.

Operation of the laser treatment apparatus having the above structure will be described below.

Explanation is first made on alignment of an irradiation area (scanning area) of the treatment beam with respect to a target treatment part. When an aiming beam irradiation switch or button on the control panel 3 is pressed, the aiming beam is irradiated from the emission end unit 30. This aiming beam is repeatedly scanned in accordance with a selected scanning pattern by operation of the first and second mirrors 33 and 34. While viewing the monitor 2 to observe both the image of a wide area taken by the camera 29 and the magnified image of the treatment part taken by the camera 31 and check the treatment part and the irradiation area (scanning area) of the aiming beam, an operator operates the switches 4b and 4c to align the irradiation area of the aiming beam to the target treatment part. In response to signals from the switches 4b and 4c, the control section 15 drives the movement mechanism 25 to move the emission end unit 30 in the X- and Y-directions respectively. Also, when the joystick 4 is operated to tilt back, forth, right, or left, the control section 15 drives the movement mechanism 21 to change the inclination angle of the emission end unit 30 in the X- and Y-directions so that the inclination angle of the laser emission direction becomes proper with respect to the treatment part. Thus, positional alignment is completed.

Distance alignment of the emission end unit 30 in the laser emission direction is performed in the following manner.

The distance from the unit 30 to the skin surface is detected by the sensor sections 4a–4d. Based on the detection result, accordingly, the control section 15 drives the movement mechanism 80 to move the emission end unit 30 in the Z-direction so that the treatment beam comes into a focus on the skin surface. Alternatively, the movement mechanism 80 may be driven by operation of a focus switch (button) on the control panel 3 so that the image taken by the camera 31 (or 29) is displayed in focus on the monitor 2.

Furthermore, the sensor sections 40a–40d are also used as the inclination sensor. With the information from those sensor sections 40a–40d, the laser emission direction of the emission end unit 30 may automatically be aligned to be substantially perpendicular with respect to the skin surface. This automatic perpendicular alignment of the laser emission direction is explained below with reference to FIG. 8. The present embodiment takes as an example the case where the skin surface to be subjected to the laser irradiation is slant only in the X-direction.

Figure 8A:
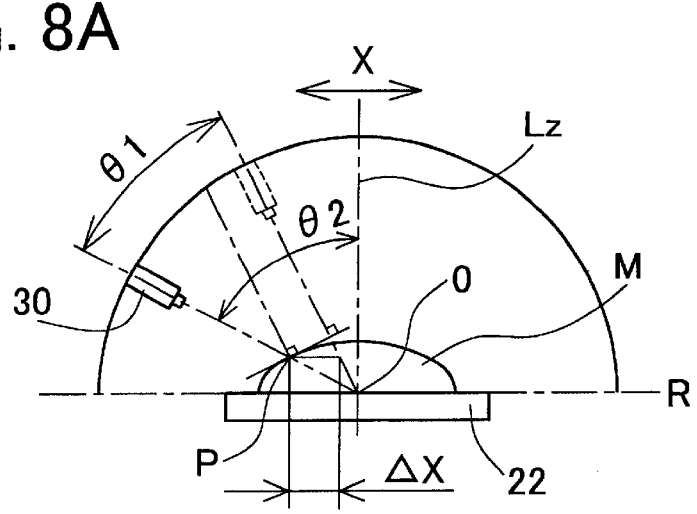
FIGS. 8A–8C are explanatory views showing away of determining a position to be irradiated with a laser beam for treatment.

The joystick 4 and the like is operated as above to align the irradiation position of the aiming beam (a spot position in the optical axis direction of the lens 37) to a target irradiating point P on a patient's body M, as shown in FIG. 8A. At this time, it is assumed that the emission end unit 30 is inclined by an angle θ2 with respect to a vertical reference line Lz passing a reference point O which is a center of a circle configuring the arm 23. The operator then presses a confirmation switch (button) on the control panel 3. The emission direction needs to be substantially perpendicular to the skin surface at the irradiating point P. Therefore the control section 15 detects the slant angle of the skin surface based on the detection signals from the four sets of sensor sections 40a–40d, thus determining a correction angle θ1 of the laser emission direction (a correction angle in the X-direction). Simultaneously, the control section 15 determines the distance between the emission end unit 30 and the irradiating point P based on the detection signals from the sensor sections 40a–40d, thus obtaining positional information of the irradiating point P with respect to the reference point O based on the determined distance and the angle θ2. It is to be noted that the distance between the emission end unit 30 and the irradiating point P may be an average of the detected distances by the four sets of sensor sections 40a–40d respectively.

Figure 8B:
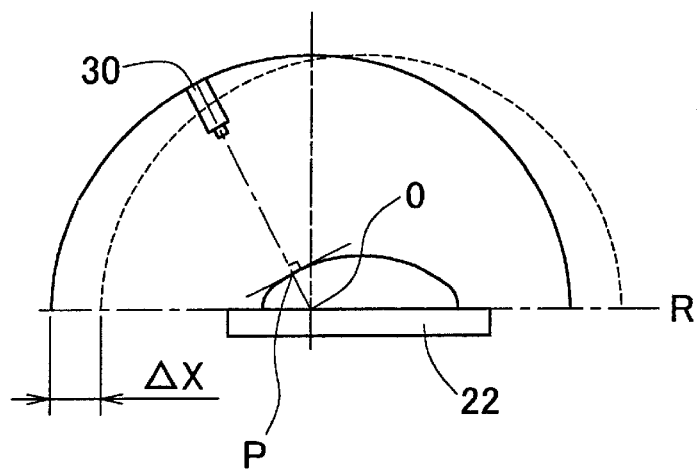

After obtaining the positional information as above, the control section 15 drives the movement mechanism 21 to change the inclination angle of the emission end unit 30 by the correction angle θ1, thereby adjusting the laser emission direction of the unit 30 to become substantially perpendicular to the skin surface at the irradiating point P. To align the laser emission direction (the irradiation position of the treatment beam, or a spot position in the optical axis direction of the lens 37) to the irradiating point P, as shown in FIG. 8B, the movement mechanism 25 is driven to move the arm 23 by the distance ΔX in the X-direction parallel to a reference plane R. This distance ΔX can be determined based on the relation among the positional information of the irradiating point P, the angle θ2 determined at the press of the confirmation switch, and the correction angle θ1.

The control section 15 then drives the movement mechanism 80 in accordance with the distance information detected by the sensor sections 40a–40d, moving the emission end unit 30 to adjust the focus of laser irradiation. This movement may be started from a step shown in FIG. 8A because the distance detection is continuously performed.

As with the case of the inclination in the X-direction exemplified in the above description, the laser emission direction can automatically be aligned to be substantially perpendicular to the skin surface slant in the Y-direction.

It is to be noted that in the case where the treatment beam is not scanned, the irradiation position of the aiming beam (the spot position in the optical axis direction of the lens 37) is aligned to the treatment part for alignment of the irradiation position of the treatment beam (the spot position in the optical axis direction of the lens 37).

After completion of the alignment to the target part as described above, the footswitch 9 may be pressed to perform laser irradiation. The control section 15 causes the solenoid valve 18 to open, allowing the cooled, compressed air to be ejected from the nozzle 38, thereby cooling the treatment part (the skin surface). Through the laser irradiation optical system in the emission end unit 30, the treatment beam is irradiated to the treatment part (the skin surface) while scanning the part in a previously selected scanning pattern. If the target treatment part could not be totally irradiated by one irradiation (one scanning), the operator repeats the above mentioned operation to move the emission end unit 30, thereby performing the laser irradiation again so that the whole treatment area is irradiated.

It is to be noted that, when the treatment beam to be irradiated to the treatment part is shaped into a collimated light beam and no scanning is performed, it may eliminate the need for moving the unit 30 in the Z-direction based on the distance detection result. When the treatment beam is caused to scan even if it is a collimated light beam, however, the distance from the unit 30 to the treatment part is preferably adjusted properly.

Next, explanation is made on automatic continuous irradiation of the treatment beam with respect to the treatment part (treatment area) of a wider region.

Figure 9:
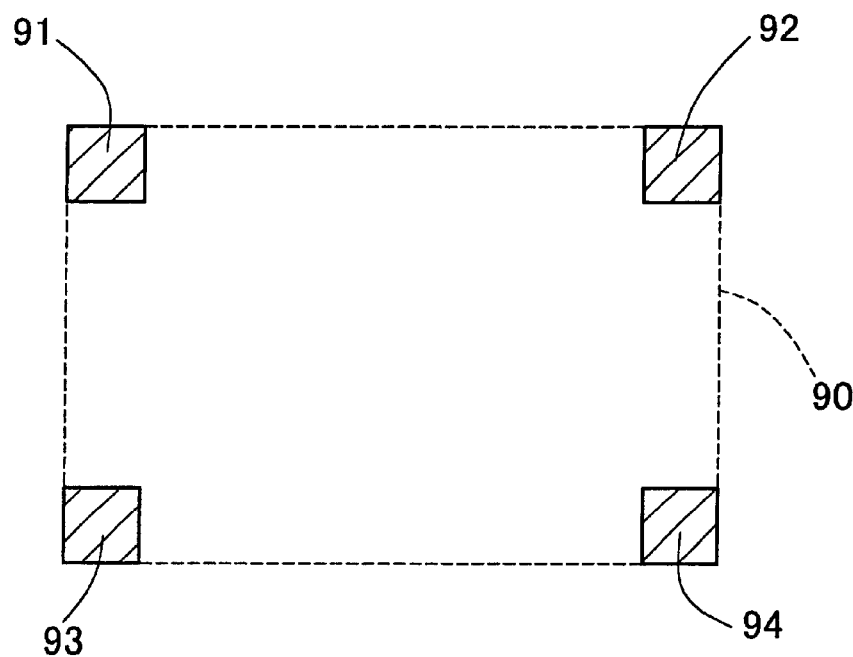
FIG. 9 is an explanatory view showing a way of determining a treatment area.

A continuous irradiation mode is first selected by press of a mode changing switch (button) on the control panel 3. Then, the treatment area to be subjected to the laser irradiation is determined in the following manner. At first, while observing the images taken by the cameras 29 and 31 and displayed on the monitor 2, as shown in FIG. 9, the operator should determine four irradiation areas 91, 92, 93, and 94 in turn at corners of a target treatment area 90. For example, the position of the irradiation area 91 is first determined as follows.

This irradiation area 91 is, as shown in FIG. 9, determined as a predetermined area (scanning area) which can be scanned by the treatment beam (and the aiming beam) irradiated from the emission end unit 30 at a place. Alternatively, this area may be an area of simply one spot (spot area).

Figure 8C:
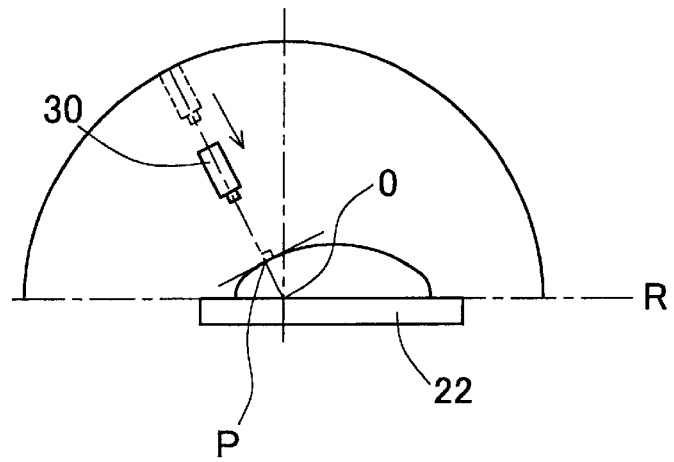

The switches 4b and 4c and the joystick 4 are operated as mentioned above to move the emission end unit 30 so that the aiming beam is irradiated to the target irradiation area 91. Thus, the unit 30 is moved into place where the treatment beam (and the aiming beam) is directed substantially perpendicular to the irradiation area 91, as shown in FIG. 8.

The confirmation switch on the control panel 3 is pressed. At this time, the control section 15 stores the position of the irradiation area 91. Each position of the other irradiation areas 92–94 is determined in the same way as above. Finally, a setting completion switch (button) on the control panel 3 is pressed to determine the treatment area 90 surrounded by the irradiation areas 91–94. Upon completion of the above setting, each of he irradiation areas is computed for laser irradiation on the whole treatment area 90.

To be more specific, the area to be irradiated in one irradiation, or the diagonally shaded area 91 in FIG. 9, is successively moved within the treatment area 90 determined as above. The treatment beam is desired to uniformly irradiate treatment area 90. In the present embodiment, therefore, as the irradiation area shifts within the treatment area 90, the dimension of each irradiation area may appropriately be increased or decreased according to the dimension of the treatment area 90 defined by the irradiation areas 91–94, avoiding overlap of the adjacent irradiation areas. Furthermore, the perpendicular relation of the treatment beam with respect to each irradiation area within the treatment area 90 during irradiation is maintained by computation with interpolation of data on the irradiation areas 91–94.

The irradiation areas are stored and controlled as the movement data of the emission end unit 30 (the positional information of the unit 30), namely, the movement data of the movement mechanism 25 and the movement mechanism 21.

After completion of the determination of the treatment area 90, under control of the control section 15, the emission end unit 30 is caused to move so that the treatment beam is irradiated to the first irradiation area 91 and the inclination angle of the unit 30 is adjusted until the laser emission direction becomes substantially perpendicular to the irradiation plane (the skin surface). Then, when the operator presses the footswitch 9, the control section 15 activates the light source section 10 and the emission end unit 30 to irradiate the treatment beam through the laser irradiation optical system to the irradiation area 91. When the laser irradiation on the irradiation area 91 is finished, the control section 15 stops activating the light source section 10 to stop the laser irradiation. Then, the control section 15 adjusts the moving position of the emission end unit 30 and the inclination angle of the laser emission direction thereof in order to irradiate the treatment beam to an adjacent irradiation area, and activates the light source section 10 again to start laser irradiation onto the irradiation area aligned as above. In this manner, for every irradiation area within the treatment area 90, the movement and the angle adjustment of the unit 30 is automatically carried out. Simultaneously, the light source section 10 is driven to control the laser irradiation so that the determined treatment area 90 is sequentially irradiated.

It is to be noted that a shutter may additionally be arranged to be insertable in the optical path of the treatment beam. This shutter is controlled to start/stop the laser irradiation on each of the irradiation areas. Alternatively, the laser irradiation may be controlled so as to stop when the operator releases the footswitch 9.

Figure 10:
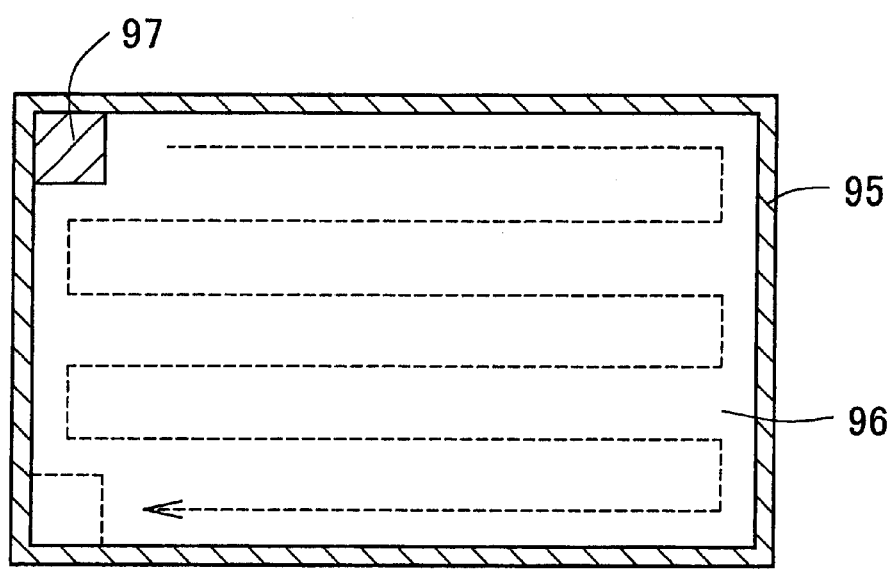
FIG. 10 is an explanatory view showing a way of continuously irradiating a treatment area specified by marking.

The determination of the treatment area and the continuous irradiation of the treatment beam may be performed in the following manner. As shown in FIG. 10, a mark 95 is drawn in ink or the like around a target treatment area 96 so as to enable discrimination of the treatment area 96 from another area not to be treated (non-treatment area). The mark 95 is extracted from the image taken by the camera 29 in an image processing part of the control section 15, and the area within the mark 95 is automatically determined as the treatment area 96. The positional relation of the irradiation area with respect to the mark 95 is controlled so that the irradiation area to be irradiated with the treatment beam from the emission end unit 30 falls within the mark 95. Correspondingly, the movement and the angle adjustment of the unit 30 are controlled. The positional relation of the irradiation area with respect to the mark 95 can be determined in the image processing to extract the aiming beam irradiation area 97 and the mark 95 from the image taken by the camera 29. When the laser irradiation is completed, the emission end unit 30 is moved to align the aiming beam irradiation area 97 to the next area to be irradiated. Then, the light source section 10 is activated to successively perform the laser irradiation.

The determination of the treatment area may be done by the image processing on the image taken by the camera 29 or 31 which photographs (images) the patient's body (skin). For instance, the color of a bed 22 may be made black to be usable instead of the discrimination mark. This black bed 22 allows judgement as to whether or not the object is a skin based on the contrast between the patient's skin and the black bed 22. Furthermore, the non-treatment area needing no laser irradiation is covered with a protective black sheet, which is utilized as a discrimination mark. The same judgement as above is made on a skin portion based on the contrast. The position and dimension of the irradiation area of the treatment beam in association with the movement of the emission end unit 30 are recognized from the previously set irradiation conditions. Therefore the movement of the unit 30 is controlled by means of the corresponding drive systems to shift the irradiation area to not-yet-irradiated areas in turn so that the treatment beam is continuously irradiated.

The above explanation is made on laser depilation. In a different case of treating birthmarks or the like which have a relatively wide area, on the other hand, the drive systems are controlled to photograph (image) a wider region so that the treatment area may be determined by discrimination from the non-treatment area.

Figure 11:
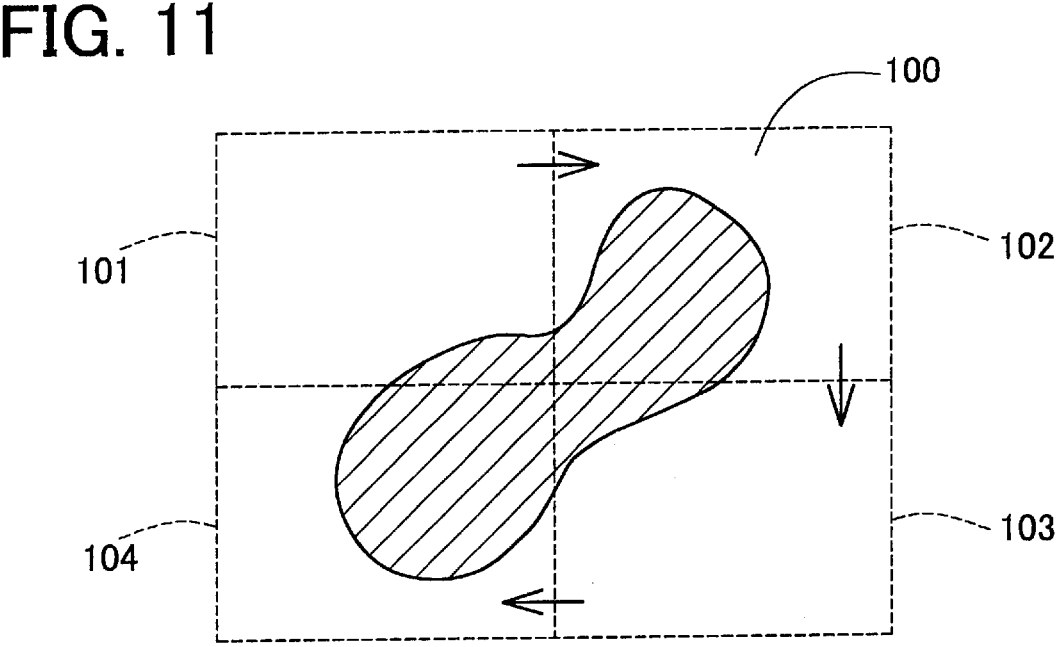
FIG. 11 is an explanatory view showing a way of photographing (imaging) a birthmark of a wide region by using a drive system.
Figure 12:
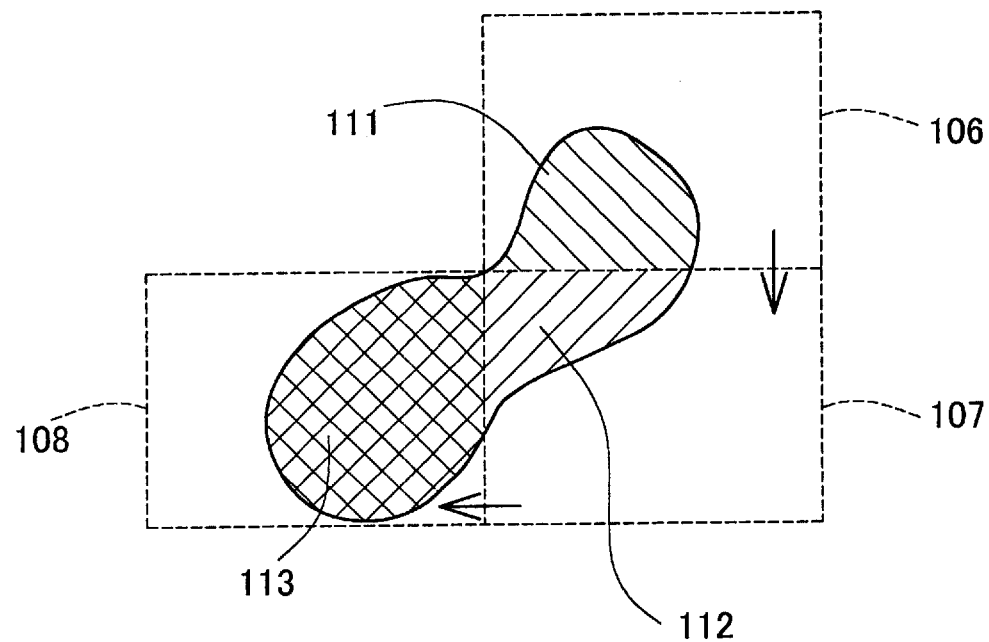
FIG. 12 is an explanatory view showing a way of performing optimum laser irradiation by using the drive system to the photographed (imaged) birthmark.

For example, the laser treatment on birthmarks is conducted in the following manner. In this case, the light source section 10 is constructed of dye lasers appropriate for birthmark treatment. As shown in FIG. 11, the drive systems are controlled to move the emission end unit 30 while the camera 31 photographs (images) a birthmark 100 in sections 101, 102, 103, and 104 in turn. More specifically, the operator operates the joystick 4 so that the treatment part (birthmark 100) in the first section 101 comes within a screen of the monitor 2. The control section 15 detects the birthmark 100 in the first section 101 based on the image signal from the camera 31 and stores the two-dimensional position of the birthmark 100 in a memory 16. The control section 15 determines a direction in which the birthmark 100 continuously extends by processing the image signal. Under control of the control section 15, the emission end unit 30 is moved in the direction in which the birthmark 100 continuously extends to the next section 102. As with above, the unit 30 is moved to the sections 103 and 104 in order. The moving position of the emission end unit 30 is determined to sequentially laser-irradiate the birthmark 100 based on the movement data (positional information) of the unit 30 at the time of photographing (imaging) in the four sections, the positional information of the treatment area determined in each photographing position, and the information on the laser irradiation area (the irradiation area 106 in FIG. 12) in each of the moving positions of the unit 30. To be more specific, as shown in FIG. 12, the irradiation position is shifted to the sections 106, 107, and 108 in turn so that the number of times the unit 30 is moved becomes minimum. Every time the unit 30 is moved to each of the irradiation areas, the control section 15 permits the laser irradiation from the light source section 10, and stops it upon completion of the predetermined laser irradiation.

In every irradiation area, the first and second mirrors 33 and 34 are driven to scan the treatment beam to irradiate only the portion where the birthmark 100 exists. In other words, the treatment beam is scanned over only a birthmark part 111 in the irradiation section 106, a birthmark part 112 in the section 107, and a birthmark part 113 in the section 108, respectively.

Since the image taken by the camera 29 is displayed on the monitor 2, the way of designating the treatment area on the screen of the monitor 2 by use of a device such as a computer mouse can also achieve the determination of the treatment area.

In this case, the irradiation area of the treatment beam is stored and managed as the area to be irradiated by the treatment beam and the data on movement of the treatment beam with respect to the treatment area determined on the screen of the monitor 2. Also, it is stored and managed as the movement data of the emission end unit 30 (the positional information of the unit 30) for directing the treatment beam perpendicular to the irradiation area, namely, the movement data of the movement mechanism 25 and the movement mechanism 21 for moving the emission end unit 30.

As described above, differently from the conventional apparatus, the apparatus in the present embodiment can eliminate the need for an operator to perform treatment by holding a hand piece by hand. This can reduce the burden on the operator. The apparatus in the present embodiment also enables for the operator to observe the treatment part in a magnified image taken by the camera 31. Therefore the condition of the treatment part can well be recognized at each stage; pre-, in-, and post-operation. Reactions of the treatment part to the laser treatment can be observed on the monitor 2.

The present invention may be embodied in other specific forms without departing from the spirit or essential characteristics thereof. For instance, the present invention is applicable, besides depilation, to the laser treatment on skins with blood-vessel troubles, pigmentation troubles (birthmarks), or others. The light source section for emitting the treatment laser beam may be selected according to treatment purposes, for example, from among a ruby laser, an alexandrite laser, an argon laser, a dye laser, a CO2 laser, and the like.

Several types of the above light sources having different wavelengths and properties may be provided together in a main body of the apparatus so that an optimum one is selected according to the kind of disease. The optical system for delivering the treatment laser beam from the light source to the laser emission end may be constructed of mirrors which reflect the treatment beam, instead of fibers.

As described above, according to the present invention, the laser irradiation can easily be performed without burden on an operator.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus for irradiating a treatment part with a laser beam for treatment, the apparatus including:

a treatment light irradiation unit including:
a treatment light source which emits the treatment laser beam;
an irradiation optical system which delivers the treatment laser beam; emitted from the light source to irradiate the treatment part, the irradiation optical system having a condensing lens which forms the treatment laser beam into a predetermined spot size on the treatment part and a scanning unit which scans the treatment laser beam two-dimensionally; and
a laser emission end unit provided with the condensing lens and the scanning unit;

a lens moving unit which moves the condensing lens in a direction of an optical axis;

a movement unit which moves the emission end unit with respect to the treatment part, the movement unit including a first movement unit which moves the guide rail with respect to the treatment part relatively and an angle chance unit which changes an irradiation angle of the emission end unit;

a determination unit which determined an irradiation position of the treatment laser beam; and a control section which transmits a control signal to the lens moving unit and the movement unit based on a determination result by the determination unit.

2. The laser treatment apparatus according to claim 1, wherein the determination unit includes a treatment part detection unit provided with an image pickup device, which detects the treatment part by taking an image of a skin of a patient and processing the image, and a determination section which determines the irradiation position of the treatment laser beam based on the detected treatment part.

3. The laser treatment apparatus according to claim 1, further including an angle detection unit which detects the irradiation angle of the emission end unit based on the determined irradiation position, and
wherein the control section transmits the control signal to at least one of the first movement unit and the angle change unit based on a detection result by the angle detection unit.

4. The laser treatment apparatus according to claim 1, further including a position detection unit which detects a focal position of the treatment laser beam with respect to the treatment part in the optical axis direction relatively based on the determined irradiation position, and
wherein the control section transmits a control signal to the lens moving unit based on a detection result by the position detection unit.

5. The laser treatment apparatus according to claim 1, wherein the second movement unit moves the guide rail in a two-dimensional direction parallel to a reference plane with respect to the treatment part relatively.

6. The laser treatment apparatus according to claim 1, wherein the lens moving unit includes a third movement which moves the emission end unit in the optical axis direction.

* * * * *